United States Patent
Inokuchi et al.

(10) Patent No.: US 8,632,791 B2
(45) Date of Patent: Jan. 21, 2014

(54) SILICONE MICROPARTICLES COMPRISING SILICONE ELASTOMER SPHERICAL MICROPARTICLES COATED WITH POLYORGANOSILSESQUIOXANE, AND METHOD OF PRODUCING SAME

(75) Inventors: Yoshinori Inokuchi, Annaka (JP); Ryuji Horiguchi, Takasaki (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 576 days.

(21) Appl. No.: 12/609,524

(22) Filed: Oct. 30, 2009

(65) Prior Publication Data

US 2010/0112023 A1    May 6, 2010

(30) Foreign Application Priority Data

Oct. 31, 2008    (JP) ................. 2008-281526

(51) Int. Cl.
*A61K 8/02*    (2006.01)
*A61K 31/00*    (2006.01)

(52) U.S. Cl.
USPC ....................... 424/401; 424/78.31

(58) Field of Classification Search
None
See application file for complete search history.

(56) References Cited

U.S. PATENT DOCUMENTS

| | | | | |
|---|---|---|---|---|
| 5,538,793 | A * | 7/1996 | Inokuchi et al. | ............... 428/407 |
| 2010/0203095 | A1 | 8/2010 | Inokuchi et al. | |
| 2011/0110994 | A1 | 5/2011 | Inokuchi et al. | |
| 2011/0117145 | A1 | 5/2011 | Inokuchi et al. | |
| 2011/0117146 | A1 | 5/2011 | Inokuchi et al. | |

FOREIGN PATENT DOCUMENTS

| | | |
|---|---|---|
| EP | 0 958 805 A2 | 11/1999 |
| EP | 0 958 805 A3 | 11/1999 |
| EP | 1 582 203 A1 | 10/2005 |
| EP | 1 777 278 A1 | 4/2007 |
| JP | 8-109262 | 4/1996 |
| JP | 2000-86427 | 3/2000 |
| JP | 2005-187379 | 7/2005 |
| JP | 2006-335978 | 12/2006 |
| WO | WO 97/04737 | 2/1997 |

OTHER PUBLICATIONS

U.S. Appl. No. 12/609,429, filed Oct. 30, 2009, Inokuchi, et al.
Office Action issued Dec. 21, 2012 in European Patent Application No. 09 013 636.7.
Japanese Office Action issued Aug. 27, 2013, in Japan Patent Application No. 2009-240812 (with English translation).
Japanese Office Action issued Jun. 4, 2013, in Japan Patent Application No. 2009-240812 (with English translation).

* cited by examiner

*Primary Examiner* — Daniel Sullivan
*Assistant Examiner* — Melissa Javier
(74) *Attorney, Agent, or Firm* — Oblon, Spivak, McClelland, Maier & Neustadt, L.L.P.

(57) ABSTRACT

Provided are silicone microparticles including 100 parts by mass of silicone elastomer spherical microparticles having a volume average particle diameter within a range from 0.1 to 100 μm, and 0.5 to 25 parts by mass of a polyorganosilsesquioxane that coats the surface of the silicone elastomer spherical microparticles, in which the silicone elastomer is capable of absorbing not less than 30 parts by mass of at least one oily substance selected from the group consisting of sebum, hydrocarbon oils and ester oils per 100 parts by mass of the silicone elastomer. These silicone microparticles are capable of absorbing a large amount of the above oily substances, are able to ameliorate various problems caused by sebum such as changes in cosmetic make-up properties, changes in the color of cosmetic materials and increased shininess of cosmetic materials, and are also able to suppress the greasiness, stickiness, and oily film feeling of cosmetic materials containing at least one of liquid oils composed of hydrocarbon oils and ester oils. The silicone microparticles can be produced by hydrolyzing and condensing an organotrialkoxysilane in a water medium, in the presence of the above silicone elastomer spherical microparticles and an alkaline material, thereby coating the surface of the silicone elastomer spherical microparticles with a polyorganosilsesquioxane.

13 Claims, No Drawings

SILICONE MICROPARTICLES COMPRISING SILICONE ELASTOMER SPHERICAL MICROPARTICLES COATED WITH POLYORGANOSILSESQUIOXANE, AND METHOD OF PRODUCING SAME

BACKGROUND OF THE INVENTION

1. Field of the Invention

The present invention relates to silicone microparticles comprising silicone elastomer spherical microparticles coated with a polyorganosilsesquioxane which are able to absorb at least one of sebum and the hydrocarbon oils and ester oils that together constitute liquid oils, and also relates to a method of producing such silicone microparticles.

2. Description of the Prior Art

Following application to the skin, cosmetic make-up materials tend to gradually change their cosmetic properties over time as a result of the sebum secreted from the skin. In other words, the cosmetic material tends to lose its adhesion to the area of skin to which it has been applied as a result of the sebum, and becomes more readily transferable to other areas of the skin or clothing upon contact with such other areas of the skin or clothing. Further, sebum tends to change the color of the cosmetic material, and also causes an increase in the shine of the cosmetic material. Accordingly, cosmetic make-up materials containing sebum-absorbing powders have been proposed (for example, see Patent Document 1). However, the sebum tends to remain adsorbed to the surface of these powders, or to become absorbed in the spaces between powder particles, and because the sebum is not absorbed into the interior of the powder particles, the amount of sebum absorbed by the powder is minimal, meaning the effect of the powder in preventing discoloration or shininess of the cosmetic material is inadequate.

On the other hand, cosmetic materials containing an added liquid oil such as a paraffin or an ester are used to impart softness and smoothness to the skin, thus providing an emollient effect, but these types of cosmetic materials suffer from the unavoidable drawbacks of greasiness, stickiness, and an oily film feeling.

Conventionally, silicone particles have been used to impart cosmetic materials with favorable feelings during use, such as a feeling of silkiness or smoothness, and also to impart improved extensibility. In particular, silicone microparticles comprising spherical microparticles of a silicone rubber coated with a polyorganosilsesquioxane (see Patent Document 2) have a soft feel, are non-cohesive, and exhibit excellent dispersibility, and are therefore used in a wide variety of cosmetic materials. However, the coated silicone microparticles disclosed specifically in Patent Document 2 comprise a core of a silicone rubber spherical microparticle formed from a cured product of a silicone that comprises only lower alkyl groups as the organic groups bonded to the silicon atoms, and no mention is made of silicone microparticles capable of absorbing a large amount of at least one of sebum and liquid oils.

[Patent Document 1] WO 97/04737
[Patent Document 2] U.S. Pat. No. 5,538,793

SUMMARY OF THE INVENTION

An object of the present invention is to provide silicone microparticles that are capable of absorbing a large amount of at least one of sebum and the hydrocarbon oils and ester oils that together constitute liquid oils, are able to ameliorate various problems caused by sebum such as changes in cosmetic make-up properties, changes in the color of cosmetic materials and increased shininess of cosmetic materials, and are also able to suppress the greasiness, stickiness, and oily film feeling of cosmetic materials containing at least one of the above liquid oils. Another object of the present invention is to provide a method of producing such silicone microparticles.

As a result of intensive research, the inventors of the present invention discovered that the above objects could be achieved by using the silicone microparticles described below, and inventors were therefore able to complete the present invention.

In other words, a first aspect of the present invention provides:

silicone microparticles comprising 100 parts by mass of silicone elastomer spherical microparticles having a volume average particle diameter within a range from 0.1 to 100 µm, and 0.5 to 25 parts by mass of a polyorganosilsesquioxane that coats the surface of the silicone elastomer spherical microparticles, wherein the silicone elastomer is capable of absorbing not less than 30 parts by mass of at least one oily substance selected from the group consisting of sebum, hydrocarbon oils and ester oils per 100 parts by mass of the silicone elastomer.

A second aspect of the present invention provides a method of producing the silicone microparticles described above, the method comprising:

hydrolyzing and condensing an organotrialkoxysilane in a water medium, in the presence of silicone elastomer spherical microparticles having a volume average particle diameter within a range from 0.1 to 100 µm and an alkaline material, thereby coating the surface of the silicone elastomer spherical microparticles with a polyorganosilsesquioxane, wherein the silicone elastomer is capable of absorbing not less than 30 parts by mass of at least one oily substance selected from the group consisting of sebum, hydrocarbon oils and ester oils per 100 parts by mass of the silicone elastomer.

A third aspect of the present invention provides a method of absorbing at least one oily substance selected from the group consisting of sebum, hydrocarbon oils and ester oils, the method comprising:

bringing the oily substance into contact with the silicone microparticles described above, and absorbing the oily substance into the silicone microparticles.

A fourth aspect of the present invention provides use of the above silicone microparticles as an absorbent for at least one oily substance selected from the group consisting of sebum, hydrocarbon oils and ester oils.

The silicone microparticles of the present invention are capable of absorbing a large amount of at least one of sebum and the hydrocarbon oils and ester oils that together constitute liquid oils. Accordingly, it is expected that these silicone microparticles will be able to ameliorate various problems caused by sebum by providing effects such as suppression of changes in cosmetic make-up properties, suppression of changes in the color of cosmetic materials, and prevention of shininess of cosmetic materials. Furthermore, the silicone microparticles are also expected to provide other effects, including suppressing the greasiness, stickiness, and oily film feeling of cosmetic materials containing at least one of the above liquid oils.

DETAILED DESCRIPTION OF THE PREFERRED EMBODIMENTS

A more detailed description of the present invention is provided below. In the following description, viscosity values refer to kinetic viscosity values measured at 25° C. using an Ostwald viscometer.

[Silicone Elastomer Spherical Microparticles]

In the silicone microparticles of the present invention, the silicone elastomer spherical microparticles that are surface-coated with a polyorganosilsesquioxane have a volume average particle diameter that is within a range from 0.1 to 100 µm, and preferably from 1 to 40 µm. If this volume average particle diameter is less than 0.1 µm, then the resulting silicone microparticles are less likely to exhibit the desired silkiness and smoothness. If the volume average particle diameter exceeds 100 µm, then the degree of silkiness and smoothness of the resulting silicone microparticles tends to deteriorate, and a feeling of grittiness may also develop. The volume average particle diameter is measured using a Coulter counter method. Further, in this description, the term "spherical" includes not only microparticles having a perfectly spherical shape, but also microparticles having deformed spherical shapes in which the average of the ratio (length of longest axis)/(length of shortest axis) (namely, the aspect ratio) is typically within a range from 1 to 4, preferably from 1 to 2, more preferably from 1 to 1.6, and still more preferably from 1 to 1.4. The shapes of the microparticles can be confirmed by inspecting the microparticles under an optical microscope.

The silicone elastomer that constitutes the silicone elastomer spherical microparticles preferably exhibits no stickiness, and preferably has a rubber hardness, measured using an Asker C hardness meter prescribed in the Society of Rubber Industry, Japan Standard (SRIS) 0101, that is within a range from 10 to 95, and more preferably from 20 to 85. Provided the rubber hardness is within a range from 10 to 95, cohesion of the obtained silicone microparticles can be adequately suppressed, and microparticles having excellent levels of flowability and dispersibility, and superior feelings of silkiness, smoothness and softness can be obtained.

The silicone elastomer is capable of absorbing not less than 30 parts by mass, and preferably at least 40 parts by mass, of at least one oily substance selected from the group consisting of sebum, hydrocarbon oils and ester oils per 100 parts by mass of the silicone elastomer. If the amount of the oily substance absorbed is less than 30 parts by mass, then the effects of the obtained silicone microparticles in suppressing changes in the cosmetic make-up properties, and suppressing the greasiness, stickiness, and oily film feeling of cosmetic materials containing at least one of liquid oils composed of hydrocarbon oils and ester oils tend to weaken. The greater the amount of oily substance absorbed the better, and therefore there are no particular limitations on the upper limit for the absorption amount, although for practical reasons, the absorption amount may be, for example, not more than 500 parts by mass, and particularly not more than 300 parts by mass.

The hydrocarbon oils and ester oils mentioned above, which represent oily substances other than sebum, are used as raw materials in some cosmetic products. Examples of the hydrocarbon oils include linear and branched hydrocarbon oils, and include both volatile hydrocarbon oils and non-volatile hydrocarbon oils. Specific examples of these hydrocarbon oils include squalanes such as synthetic squalane and plant-based squalane, squalene, light liquid isoparaffin, liquid paraffin, liquid isoparaffin, and hydrogenated isopolybutene. Specific examples of the ester oils include diethylhexyl succinate, diethylhexyl sebacate, dibutyloctyl sebacate, diisocetyl adipate, diisostearyl malate, di-2-heptylundecyl adipate, propylene glycol dicaprate, neopentyl glycol dicaprate, trimethylolpropane triethylhexanoate, pentaerythritol tetraethylhexanoate, ethyl linoleate, isopropyl isostearate, isopropyl linoleate, butyl stearate, octyl palmitate, ethylhexyl palmitate, ethylhexyl stearate, decyl oleate, myristyl myristate, cetyl ethylhexanoate, cetyl octanoate, cetyl palmitate, isocetyl dimethyloctanoate, isocetyl myristate, isocetyl palmitate, isocetyl stearate, isocetyl isostearate, isostearyl palmitate, octyldodecyl neopentanoate, octyldodecyl oleate, and octyldodecyl myristate.

The silicone elastomer is preferably a cured product of a liquid silicone composition comprising:

(A)

(A1) an organohydrogenpolysiloxane having two hydrogen atoms bonded to silicon atoms within each molecule, represented by an average composition formula (1) shown below:

$$R^1_a H_b SiO_{(4-a-b)/2} \quad (1)$$

(wherein $R^1$ represents an unsubstituted or substituted monovalent hydrocarbon group of 1 to 30 carbon atoms excluding aliphatic unsaturated groups, and a and b are positive numbers that satisfy $0<a<3$, $0<b\leq 3$, and $0.1\leq a+b\leq 3$), (A2) an organohydrogenpolysiloxane represented by the above average composition formula (1) and having at least three hydrogen atoms bonded to silicon atoms within each molecule, or a combination of component (A1) and component (A2), (B)

(B1) an organopolysiloxane having two monovalent olefinic unsaturated groups within each molecule, represented by an average composition formula (2) shown below:

$$R^2_c R^3_d SiO_{(4-c-d)/2} \quad (2)$$

(wherein $R^2$ represents an unsubstituted or substituted monovalent hydrocarbon group of 1 to 30 carbon atoms excluding aliphatic unsaturated groups, $R^3$ represents a monovalent olefinic unsaturated group of 2 to 6 carbon atoms, and c and d are positive numbers that satisfy $0<c<3$, $0<d\leq 3$, and $0.1\leq c+d\leq 3$), (B2) an organopolysiloxane represented by the above average composition formula (2) and having at least three monovalent olefinic unsaturated groups within each molecule, or a combination of component (B1) and component (B2), in an amount that yields from 0.5 to 2 monovalent olefinic unsaturated groups within component (B) per hydrogen atom bonded to a silicon atom within component (A), and (C) a platinum group metal-based catalyst, wherein from 5 to 70 mol % of at least one of $R^1$ and $R^2$ are monovalent hydrocarbon groups of 6 to 30 carbon atoms, provided that when component (A) is component (A1), component (B) is either component (B2) or a combination of component (B1) and component (B2).

Component (A)

The component (A) is an organohydrogenpolysiloxane represented by the above average composition formula (1) which comprises hydrogen atoms bonded to silicon atoms (hereafter also referred to as "SiH groups") within each molecule. The component (A) may be either the component (A1), the component (A2), or a combination of the component (A1) and the component (A2). The component (A1) and the component (A2) may each employ either a single compound or a combination of two or more compounds.

Preferably, a and b are positive numbers that satisfy $0<a\leq 2.295$, $0.005\leq b\leq 2.3$, and $0.5\leq a+b\leq 2.3$.

The number of carbon atoms within $R^1$ is typically within a range from 1 to 30, and is preferably from 1 to 22, and more preferably from 1 to 18. Specific examples of $R^1$ include alkyl groups such as a methyl group, ethyl group, propyl group, butyl group, pentyl group, hexyl group, heptyl group, octyl group, decyl group, undecyl group, dodecyl group, tetradecyl group, pentadecyl group, hexadecyl group, heptadecyl group, octadecyl group, nonadecyl group, icosyl group, henicosyl group, docosyl group, tricosyl group, tetracosyl group or triacontyl group; aryl groups such as a phenyl group, tolyl group or naphthyl group; aralkyl groups such as a benzyl group or phenethyl group; cycloalkyl groups such as a cyclopentyl group, cyclohexyl group or cycloheptyl group; and monovalent hydrocarbon groups in which some or all of the hydrogen atoms bonded to carbon atoms in any of the above groups have been substituted with either one or both of an atom such as a halogen atom (such as a fluorine atom, chlorine atom, bromine atom or iodine atom), and a substituent such as an acryloyloxy group, methacryloyloxy group, epoxy group, glycidoxy group or carboxyl group.

The viscosity of the organohydrogenpolysiloxane of component (A) is preferably not more than 100,000 mm$^2$/s, and is more preferably 10,000 mm$^2$/s or less. Provided this viscosity is not more than 100,000 mm$^2$/s, the production method described below can be used to particularly easily generate silicone microparticles having a narrow particle size distribution. Although there are no particular limitations on the lower limit for the viscosity, for practical reasons the viscosity may be, for example, at least 0.4 mm$^2$/s, and particularly 2 mm$^2$/s or greater. Furthermore, although the structure of the organohydrogenpolysiloxane of the component (A) may be a linear, cyclic or branched structure, a linear structure is particularly desirable.

Component (B)

The component (B) is an organopolysiloxane represented by the above average composition formula (2) which comprises monovalent olefinic unsaturated groups within each molecule. The component (B) may be either the component (B1), the component (B2), or a combination of the component (B1) and the component (B2). The component (B1) and the component (B2) may each employ either a single compound or a combination of two or more compounds.

Preferably, c and d are positive numbers that satisfy $0 < c \leq 2.295$, $0.005 \leq d \leq 2.3$, and $0.5 \leq c+d \leq 2.3$.

The number of carbon atoms within R$^2$ is typically within a range from 1 to 30, and is preferably from 1 to 22, and more preferably from 1 to 18. Specific examples of R$^2$ include the same groups as those exemplified above for R$^1$. As mentioned above, from 5 to 70 mol % of at least one of R$^1$ and R$^2$ represent monovalent hydrocarbon groups of 6 to 30 carbon atoms, and from 8 to 60 mol % preferably represent monovalent hydrocarbon groups of 6 to 30 carbon atoms. If this proportion of monovalent hydrocarbon groups of 6 to 30 carbon atoms is less than 5 mol %, then the absorption amount of the above oily substances tends to decrease. In contrast, if the proportion exceeds 70 mol %, then the reactivity of the organohydrogenpolysiloxane of component (A) and the olefinic unsaturated group-containing organopolysiloxane of component (B) tends to deteriorate, and the rubber hardness of the resulting cured product tends to decrease. From the viewpoint of reactivity, when 5 to 70 mol % of at least one of R$^1$ and R$^2$ represent monovalent hydrocarbon groups of 6 to 30 carbon atoms, the remaining 30 to 95 mol % of the at least one of R$^1$ and R$^2$ preferably represent methyl groups, and when 8 to 60 mol % of at least one of R$^1$ and R$^2$ represent monovalent hydrocarbon groups of 6 to 30 carbon atoms, the remaining 40 to 92 mol % of the at least one of R$^1$ and R$^2$ preferably represent methyl groups.

The number of carbon atoms with R$^3$ is typically from 2 to 6. Specific examples of R$^3$ include a vinyl group, allyl group, propenyl group, butenyl group, pentenyl group or hexenyl group. From an industrial perspective, a vinyl group is preferred.

The viscosity of the olefinic unsaturated group-containing organopolysiloxane of component (B) is preferably not more than 100,000 mm$^2$/s, and is more preferably 10,000 mm$^2$/s or less. Provided this viscosity is not more than 100,000 mm$^2$/s, the production method described below can be used to particularly easily generate silicone microparticles having a narrow particle size distribution. Although there are no particular limitations on the lower limit for the viscosity, for practical reasons the viscosity may be, for example, at least 0.7 mm$^2$/s, and particularly 2 mm$^2$/s or greater. Furthermore, although the structure of the olefinic unsaturated group-containing organopolysiloxane of the component (B) may be a linear, cyclic or branched structure, a linear structure is particularly desirable.

When the component (A) is component (A1), the component (B) is either component (B2) or a combination of component (B1) and component (B2). In other words, the combination where the component (A) is component (A1) and the component (B) is component (B1) is excluded from the combinations of component (A) and component (B) used for obtaining the silicone elastomer described above. This is because the elastomer cured product obtained from this combination tends to be prone to developing stickiness.

As mentioned above, the blend amount of the component (B) yields from 0.5 to 2 monovalent olefinic unsaturated groups within component (B) per SiH group within component (A), and this number of monovalent olefinic unsaturated groups is preferably from 0.7 to 1.5. If an amount of the component (B) that yields fewer than 0.5 or more than 2 monovalent olefinic unsaturated groups is added to the liquid silicone composition, then the resulting elastomer cured product tends to develop stickiness, and also tends to exhibit reaction activity that is overly high.

Component (C)

The platinum group metal-based catalyst of the component (C) is a catalyst that promotes the addition reaction between the SiH groups within the component (A) and the monovalent olefinic unsaturated groups within the component (B). The component (C) may use either a single catalyst or a combination of two or more different catalysts.

Any of the conventional catalysts used in hydrosilylation reactions may be used as the component (C), and specific examples include platinum group metals such as platinum (including platinum black), rhodium and palladium; platinum chlorides, chloroplatinic acids and chloroplatinates such as $H_2PtCl_4 \cdot kH_2O$, $H_2PtCl_6 \cdot kH_2O$, $NaHPtCl_6 \cdot kH_2O$, $KHPtCl_6 \cdot kH_2O$, $Na_2PtCl_6 \cdot kH_2O$, $K_2PtCl_4 \cdot kH_2O$, $PtCl_4 \cdot kH_2O$, $PtCl_2$ and $Na_2HPtCl_4 \cdot kH_2O$ (wherein, k represents an integer of 0 to 6, and is preferably either 0 or 6); alcohol-modified chloroplatinic acid (see U.S. Pat. No. 3,220,972); complexes of chloroplatinic acid and olefins (see U.S. Pat. No. 3,159,601, 3,159,662 and U.S. Pat. No. 3,775,452); a platinum group metal such as platinum black or palladium supported on a carrier such as alumina, silica or carbon; rhodium-olefin complexes; chlorotris(triphenylphosphine)rhodium (Wilkinson's catalyst); and complexes of a platinum chloride, a chloroplatinic acid or a chloroplatinate with a vinyl group-containing siloxane and particularly a vinyl group-containing cyclic siloxane.

The blend amount of the component (C) need only be sufficient to function as an effective hydrosilylation reaction catalyst, and the mass of the platinum group metal within the component (C) relative to the total mass of the composition, is typically within a range from 0.1 to 500 ppm, and is preferably from 0.5 to 200 ppm, and more preferably from 1 to 100 ppm.

Method of Producing Silicone Elastomer Spherical Microparticles

The silicone elastomer spherical microparticles can be produced in the form of a water dispersion using conventional methods. One possible method involves adding a surfactant and water to a mixed solution of an organohydrogenpolysiloxane and an olefinic unsaturated group-containing organopolysiloxane, performing an emulsification to generate an emulsion, and then adding a platinum group metal-based catalyst to initiate an addition reaction.

In this method, an example of the organohydrogenpolysiloxane is the component (A) described above, an example of the olefinic unsaturated group-containing organopolysiloxane is the component (B), and an example of the platinum group metal-based catalyst is the component (C).

Further, there are no particular restrictions on the surfactant, and examples include nonionic surfactants such as polyoxyethylene alkyl ethers, polyoxyethylene polyoxypropylene alkyl ethers, polyoxyethylene alkylphenyl ethers, polyethylene glycol aliphatic acid esters, sorbitan aliphatic acid esters, polyoxyethylene sorbitan aliphatic acid esters, polyoxyethylene sorbitol aliphatic acid esters, glycerol aliphatic acid esters, polyoxyethylene glycerol aliphatic acid esters, polyglycerol aliphatic acid esters, propylene glycol aliphatic acid esters, polyoxyethylene castor oils, polyoxyethylene hardened castor oils, polyoxyethylene hardened castor oil aliphatic acid esters, polyoxyethylene alkylamines, polyoxyethylene aliphatic acid amides, polyoxyethylene-modified organopolysiloxanes, and polyoxyethylene polyoxypropylene-modified organopolysiloxanes; anionic surfactants such as alkyl sulfates, polyoxyethylene alkyl ether sulfates, polyoxyethylene alkylphenyl ether sulfates, N-acyltaurinates, alkylbenzene sulfonates, polyoxyethylene alkylphenyl ether sulfonates, α-olefin sulfonates, alkylnaphthalene sulfonates, alkyl diphenyl ether disulfonates, dialkyl sulfosuccinates, monoalkyl sulfosuccinates, polyoxyethylene alkyl ether sulfosuccinates, aliphatic acid salts, polyoxyethylene alkyl ether acetates, N-acylamino acid salts, alkenylsuccinates, alkyl phosphates, polyoxyethylene alkyl ether phosphates, polystyrene sulfonates, formalin condensates of naphthalene sulfonic acid, formalin condensates of aromatic sulfonic acids, carboxylic acid polymers, and styrene oxyalkylene acid anhydride copolymers; cationic surfactants such as alkyltrimethylammonium salts, dialkyldimethylammonium salts, polyoxyethylene alkyldimethylammonium salts, dipolyoxyethylene alkylmethylammonium salts, tripolyoxyethylene alkylammonium salts, alkylbenzyldimethylammonium salts, alkylpyridinium salts, monoalkylamine salts, monoalkylamide amine salts, and cationized cellulose; and amphoteric surfactants such as alkyl dimethylamine oxides, alkyl dimethylcarboxybetaines, alkylamide propyl dimethylcarboxybetaines, alkyl hydroxysulfobetaines, and alkylcarboxymethyl hydroxyethyl imidazolinium betaines. These surfactants may be used individually, or two or more different surfactants may be used in combination. An anionic surfactant and a cationic surfactant may not be used in combination.

The emulsification can be performed using a typical emulsification disperser, examples of which include high-speed rotational centrifugal radial stirrers such as a homodisper, high-speed rotational shearing stirrers such as a homomixer, high-pressure injection-type emulsification dispersers such as a homogenizer, colloid mills, and ultrasonic emulsifiers.

In those cases where the platinum group metal-based catalyst exhibits poor dispersibility within water, the catalyst is preferably dissolved in a surfactant prior to addition to the emulsion. Examples of this surfactant include the same surfactants as those exemplified above.

The addition reaction may be conducted at room temperature, although in those cases where the reaction does not proceed to completion at room temperature, the reaction may be conducted under heating at a temperature of less than 100° C.

[Polyorganosilsesquioxane]

The silicone microparticles of the present invention are composed of silicone elastomer spherical microparticles coated with a polyorganosilsesquioxane, and the amount of the polyorganosilsesquioxane is typically within a range from 0.5 to 25 parts by mass, and preferably from 1 to 15 parts by mass, per 100 parts by mass of the silicone elastomer spherical microparticles described above. If the amount of the polyorganosilsesquioxane is less than 0.5 parts by mass, then the resulting silicone microparticles tend to exhibit powerful cohesiveness, and the flowability, dispersibility, silkiness and smoothness of the microparticles tend to deteriorate. In contrast, if the amount of the polyorganosilsesquioxane exceeds 25 parts by mass, then the resulting silicone microparticles tend to lose their feeling of softness, and the absorption amounts of sebum and liquid oils such as hydrocarbon oils and ester oils tend to decrease.

In the silicone microparticles of the present invention, the surface of the silicone elastomer spherical microparticles is not coated with the polyorganosilsesquioxane in such a manner that leaves absolutely no gaps in the coating. If the coating is formed with absolutely no gaps, then the silicone elastomer spherical microparticles are no longer able to absorb sebum and liquid oils. By using the production method outlined below, surface-coated silicone microparticles can be obtained in which the surface coating includes gaps that are sufficient to allow passage of at least one of sebum and the hydrocarbon oils and ester oils that together constitute liquid oils.

The polyorganosilsesquioxane preferably contains an alkyl group that is substituted with an unsubstituted or substituted amino group.

Examples of the polyorganosilsesquioxane include polymers comprising units represented by the formula $R^4SiO_{3/2}$ (wherein $R^4$ represents an unsubstituted or substituted monovalent hydrocarbon group of 1 to 20 carbon atoms, and preferably 1 to 6 carbon atoms). Specific examples of $R^4$ include alkyl groups such as a methyl group, ethyl group, propyl group, butyl group, pentyl group, hexyl group, heptyl group, octyl group, decyl group, undecyl group, dodecyl group, tetradecyl group, pentadecyl group, hexadecyl group, heptadecyl group, octadecyl group, nonadecyl group or icosyl group; alkenyl groups such as a vinyl group or allyl group; aryl groups such as a phenyl group, tolyl group or naphthyl group; aralkyl groups such as a benzyl group or phenethyl group; cycloalkyl groups such as a cyclopentyl group, cyclohexyl group or cycloheptyl group; and monovalent hydrocarbon groups in which some or all of the hydrogen atoms bonded to carbon atoms in any of the above groups have been substituted with either one or both of an atom such as a halogen atom (such as a fluorine atom, chlorine atom, bromine atom or iodine atom) and a substituent such as an unsubstituted or substituted amino group, acryloyloxy group, methacryloyloxy group, epoxy group, glycidoxy group, mercapto group or carboxyl group.

Examples of the substituted amino group mentioned above include amino groups that have been substituted with an unsubstituted or substituted monovalent hydrocarbon group of 1 to 20 carbon atoms, and preferably 1 to 6 carbon atoms. Here, examples of the unsubstituted or substituted monovalent hydrocarbon group of 1 to 20 carbon atoms include the same monovalent hydrocarbon groups as those exemplified above for $R^4$. Specific examples of the substituted amino group include the groups listed below.

—NHC$_2$H$_4$NH$_2$, —(NHC$_2$H$_4$)$_2$NH$_2$, —(NHC$_2$H$_4$)$_3$NH$_2$, —NHCH$_3$, —NHC$_2$H$_4$NHCH$_3$, —NHC$_6$H$_5$, and —NHCH$_2$C$_6$H$_5$ In order to obtain silicone microparticles of the present invention using the production method described below, not less than 50 mol % (namely, 50 to 100 mol %), and particularly 80 mol % or more (namely, 80 to 100 mol %) of all the $R^4$ groups within the polyorganosilsesquioxane are preferably methyl groups. Furthermore, the polyorganosilsesquioxane preferably contains alkyl groups that are substituted with unsubstituted or substituted amino groups, and not more than 20 mol % (namely, 0 to 20 mol %), and particularly 0.5 to 10 mol % of all the $R^4$ groups are preferably alkyl groups that are substituted with unsubstituted or substituted amino groups. Particularly, in those cases where the $R^4$ groups consist of methyl groups and alkyl groups that are substituted with unsubstituted or substituted amino groups (provided the total thereof is 100 mol %), not less than 80 mol % (namely, 80 to 100 mol %) of all the $R^4$ groups are preferably methyl groups, and not more than 20 mol % (namely, 0 to 20 mol %) of all the $R^4$ groups are preferably alkyl groups that are substituted with unsubstituted or substituted amino groups. In the same cases, 90 to 99.5 mol % of all the $R^4$ groups are more preferably methyl groups, and 0.5 to 10 mol % of all the $R^4$ groups are more preferably alkyl groups that are substituted with unsubstituted or substituted amino groups.

Specific examples of the alkyl groups that are substituted with unsubstituted or substituted amino groups are shown below, although the following is in no way an exhaustive list.

—CH$_2$NH$_2$, —C$_3$H$_6$NH$_2$, —C$_3$H$_6$NHC$_2$H$_4$NH$_2$, —C$_3$H$_6$(NHC$_2$H$_4$)$_2$NH$_2$, —C$_3$H$_6$(NHC$_2$H$_4$)$_3$NH$_2$, —C$_3$H$_6$NHCH$_3$, —C$_3$H$_6$NHC$_2$H$_4$NHCH$_3$, —C$_3$H$_6$NHC$_6$H$_5$, and —C$_3$H$_6$NHCH$_2$C$_6$H$_5$ Furthermore, the polyorganosilsesquioxane may also include, besides the $R^4SiO_{3/2}$ units, at least one type of unit selected from among $R^4{_2}SiO_{2/2}$ units, $R^4{_3}SiO_{1/2}$ units and $SiO_{4/2}$ units (wherein $R^4$ is as defined above), provided the inclusion of this other type of unit does not impair the favorable feelings during use of the obtained silicone microparticles, such as feelings of silkiness or smoothness, nor impair the other properties of the silicone microparticles such as the soft feeling, the lack of cohesiveness, and the dispersibility. In this type of polyorganosilsesquioxane, the proportion of $R^4SiO_{3/2}$ units within the total number of all siloxane units is preferably within a range from 70 to 100 mol %, and is more preferably from 80 to 100 mol %.

[Production Method]

The coating of the surface of a particle with another material belongs to the field of particle complexing techniques, and numerous methods have been proposed for achieving this type of coating. Examples of such methods include methods in which particles that act as the core (hereafter referred to as "core particles") and particles that are used for coating the surface of the core particles (hereafter referred to as "coating material particles") are subjected to dry mixing, thereby adhering the coating material particles to the surface of the core particles, and methods in which the dry mixed particles are subsequently subjected to processing that imparts an impact force, a compressive force, a frictional force or a shearing force or the like to the particles, thereby fixing the coating material particles to the surface of the core particles in the form of a film. However, because silicone elastomer particles exhibit powerful cohesion, adhering a uniform thin film of coating material particles to the surface of the silicone elastomer particles by dry mixing is problematic. Further, because the silicone elastomer particles also exhibit elasticity, the coating material particles cannot be satisfactorily fixed to the surface of the silicone elastomer particles even if an impact force, a compressive force, a frictional force or a shearing force or the like is applied to the particles. Another method exists that involves producing the coated particles by spray drying a dispersion of the core particles and the coating material particles, but this method tends to also produce aggregated particles, particles composed solely of the coating material particles, or both these types of particles.

Accordingly, the silicone microparticles of the present invention are preferably produced using the method disclosed in Patent Document 2. In other words, the silicone microparticles are preferably produced by hydrolyzing and condensing an organotrialkoxysilane in a water medium, in the presence of the aforementioned silicone elastomer spherical microparticles having a volume average particle diameter within a range from 0.1 to 100 μm and an alkaline material, thereby coating the surface of the silicone elastomer spherical microparticles with a polyorganosilsesquioxane. The water medium, the silicone elastomer spherical microparticles, the alkaline material and the organotrialkoxysilane may be either added simultaneously or added at different times, although from the viewpoint of reactivity, the organotrialkoxysilane is preferably added to a water dispersion of the silicone elastomer spherical microparticles that already contains the added alkaline material.

The alkaline material functions as a catalyst for the hydrolysis-condensation reaction of the organotrialkoxysilane. The alkaline material may be either a single material or a combination of two or more different materials. The alkaline material may be either added as is, or added in the form of an alkaline aqueous solution. The amount added of the alkaline material is adjusted so that the pH of the water dispersion of the silicone elastomer spherical microparticles containing the alkaline material is preferably within a range from 10.0 to 13.0, and more preferably from 10.5 to 12.5. Provided the amount of the alkaline material yields a pH within a range from 10.0 to 13.0, the hydrolysis-condensation reaction of the organotrialkoxysilane, and the coating of the surface of the silicone elastomer spherical microparticles by the polyorganosilsesquioxane both proceed favorably.

There are no particular restrictions on the alkaline material, and specific examples of materials that may be used include alkali metal hydroxides such as potassium hydroxide, sodium hydroxide and lithium hydroxide; alkaline earth metal hydroxides such as calcium hydroxide and barium hydroxide; alkali metal carbonates such as potassium carbonate and sodium carbonate; ammonia; tetraalkylammonium hydroxides such as tetramethylammonium hydroxide and tetraethylammonium hydroxide; and amines such as monomethylamine, monoethylamine, monopropylamine, monobutylamine, monopentylamine, dimethylamine, diethylamine, trimethylamine, triethanolamine and ethylenediamine. Of these, ammonia is the most desirable as it can be readily removed from the powder of the resulting silicone microparticles by volatilization. Commercially available aqueous solutions of ammonia may be used as the ammonia.

Examples of the organotrialkoxysilane include compounds represented by a formula: $R^4Si(OR^5)_3$ (wherein $R^4$ is as defined above, and $R^5$ represents an unsubstituted monovalent hydrocarbon group of 1 to 6 carbon atoms). Specific examples of $R^5$ include a methyl group, ethyl group, propyl group, butyl group, pentyl group or hexyl group, although in terms of reactivity, a methyl group is preferred. In those cases where it is desirable to introduce at least one type of other unit selected from among $R^4_2SiO_{2/2}$ units, $R^4_3SiO_{1/2}$ units and $SiO_{4/2}$ units into the polyorganosilsesquioxane, at least one of the corresponding compounds, namely at least one of $R^4_2Si(OR^5)_2$, $R^4_3SiOR^5$ and $Si(OR^5)_4$, respectively, may also be added. (In the above formulas, $R^4$ and $R^5$ are as defined above). In those cases where $R^4Si(OR^5)_3$, and at least one of $R^4_2Si(OR^5)_2$, $R^4_3SiOR^5$ and $Si(OR^5)_4$ (wherein $R^4$ and $R^5$ are as defined above) are used as the raw materials for the polyorganosilsesquioxane, the proportion of the $R^4Si(OR^5)_3$ within the combined total of all the raw materials is preferably within a range from 70 to 100 mol %, and is more preferably from 80 to 100 mol %.

The amount added of the organotrialkoxysilane is adjusted so that the amount of the polyorganosilsesquioxane is typically within a range from 0.5 to 25 parts by mass, and preferably from 1 to 15 parts by mass, per 100 parts by mass of the silicone elastomer spherical microparticles.

The addition of the organotrialkoxysilane is preferably performed under stirring with a typical stirring device such as a propeller blade or a flat blade or the like. The organotrialkoxysilane may be added in a single batch, but is preferably added gradually over a period of time. Further, the temperature during the addition is preferably within a range from 0 to 60° C., and is more preferably from 0 to 40° C. Provided this temperature is within a range from 0 to 60° C., the surface of the silicone elastomer spherical microparticles can be coated with the polyorganosilsesquioxane in a more favorable state.

The stirring is continued following the addition of the organotrialkoxysilane, until the hydrolysis-condensation reaction of the organotrialkoxysilane is complete. In order to complete the hydrolysis-condensation reaction, the reaction may be conducted either at room temperature or under heating at a temperature within a range from 40 to 100° C.

Following the hydrolysis-condensation reaction, water is removed from the water dispersion of the obtained silicone microparticles of the present invention. This removal of the water is performed, for example, by heating the water dispersion at normal pressure or under reduced pressure following completion of the reaction, and more specific examples include a method in which the water is removed by leaving the dispersion to stand under heat, a method in which the water is removed while the dispersion is stirred and flowed under heat, a method in which the dispersion is sprayed and dispersed in a hot air stream such as by use of a spray drier, and methods that employ a fluid heating medium. Prior to this water removal operation, a pretreatment may be used to concentrate the dispersion using a method such as thermal dehydration, separation by filtration, centrifugal separation, or decantation. Moreover, if necessary, the dispersion may be washed with water.

In those cases where the product obtained upon removal of the water from the dispersion following reaction is an aggregate, the silicone microparticles can be obtained by crushing the product using a crushing device such as a jet mill, ball mill or hammer mill.

EXAMPLES

A more detailed description of the present invention is presented below based on a series of examples and comparative examples, although the present invention is in no way limited by these examples. In the examples, unless stated otherwise, "%" values representing concentration or content refer to "% by mass". Furthermore, a "long-chain monovalent hydrocarbon group" refers to a monovalent hydrocarbon group of 6 to 30 carbon atoms, and an "amount of long-chain monovalent hydrocarbon groups" either refers to the proportion (mol %) of long-chain monovalent hydrocarbon groups to all the $R^1$ groups in the case of the organohydrogenpolysiloxane that corresponds with component (A), or refers to the proportion (mol %) of long-chain monovalent hydrocarbon groups to all the $R^2$ groups in the case of the organopolysiloxane that corresponds with component (B).

Example 1

A glass beaker with a capacity of 1 liter was charged with 400 g of an organohydrogenpolysiloxane A1 represented by formula (3) shown below and having an amount of long-chain monovalent hydrocarbon groups of 22.2 mol % and a viscosity of 110 mm²/s, and 114 g of a methylvinylpolysiloxane B1 represented by a formula (4) shown below, containing no long-chain monovalent hydrocarbon groups and having a viscosity of 10 mm²/s (equivalent to 0.96 olefinic unsaturated groups within the methylvinylpolysiloxane B1 per SiH group within the organohydrogenpolysiloxane A1), and stirring and mixing were performed at 2,000 rpm using a homomixer. To the resulting mixed liquid were added 1.0 g of a polyoxyethylene lauryl ether (number of mols of added ethylene oxide=9 mol) and 100 g of water, and subsequent stirring at 6,000 rpm using the homomixer yielded an O/W type emulsion of increased viscosity. Stirring was continued for a further 15 minutes. Subsequently, with the stirring continued at 2,000 rpm, 382 g of water was added, yielding a uniform white emulsion. This emulsion was transferred to a glass flask with a capacity of 1 liter fitted with a stirring device having an anchor-shaped stirring blade, and following adjustment of the temperature to a value of 15 to 20° C., a mixed solution containing 1.6 g of a toluene solution of a chloroplatinic acid-olefin complex (platinum content: 0.5%), 0.6 g of a polyoxyethylene lauryl ether (number of mols of added ethylene oxide=9 mol), and 0.4 g of a polyoxyethylene lauryl ether (number of mols of added ethylene oxide=4 mol) was added to the flask under constant stirring. Stirring was then continued at the same temperature for 12 hours, thus forming a water dispersion of silicone elastomer microparticles. Inspection of the shape of these silicone elastomer microparticles under an optical microscope revealed that the particles were spherical, and measurement of the volume average particle diameter using a particle size distribution measuring apparatus "Multisizer 3" (a product name, manufactured by Beckman Coulter, Inc.) yielded a result of 12 μm.

876 g of the thus obtained water dispersion of silicone elastomer spherical microparticles was transferred to a glass flask with a capacity of 3 liters fitted with a stirring device having an anchor-shaped stirring blade, and 1,988 g of water and 57 g of 28% ammonia water were added to the flask. The pH of the liquid at this point was 11.2. Following lowering of the temperature to 5 to 10° C., a mixed solution containing 76.8 g of methyltrimethoxysilane and 2.1 g of γ-aminopropyltrimethoxysilane (amounts that yield 8.7 parts by mass of a polyorganosilsesquioxane following the hydrolysis and condensation reaction per 100 parts by mass of the silicone elastomer spherical microparticles) was added dropwise to the flask over a period of 30 minutes, and stirring was then continued for a further 1 hour. During this period, the liquid temperature was maintained at 5 to 10° C. Subsequently, the reaction mixture was heated to 55 to 60° C., and stirring was continued at this temperature for 1 hour to complete the hydrolysis-condensation reaction of the above methoxysilanes.

The thus obtained methoxysilane hydrolysis-condensation reaction liquid was dewatered to a water content of approximately 30% using a pressure filtration device. The dewatered product was transferred to a stainless steel tray and dried at a temperature of 105° C. in a hot air circulating drier. The resulting dried product was crushed in a jet mill, yielding microparticles with good flowability. Inspection of these microparticles using an electron microscope revealed spherical particles, the surface of which were coated with particulate matter with a particle diameter of approximately 100 nm, confirming that silicone microparticles comprising the silicone elastomer spherical microparticles coated with a polyorganosilsesquioxane had been obtained. The thus obtained silicone microparticles were dispersed in water using a surfactant, and subsequent measurement of the volume average particle diameter using a Multisizer 3 yielded a result of 13 µm.

The organohydrogenpolysiloxane A1, the methylvinylpolysiloxane B1, and the toluene solution of a chloroplatinic acid-olefin complex (platinum content: 0.5%) were mixed together in the same proportions as those used above in preparing the silicone elastomer spherical microparticles, and the resulting mixture was poured into an aluminum Petri dish in an amount sufficient to generate a thickness of 10 mm. The mixture was left to stand at 25° C. for 24 hours, and was then heated for 1 hour in a thermostatic chamber at 50° C., thus forming a non-sticky silicone elastomer. Measurement of the hardness of this silicone elastomer using an Asker C hardness meter prescribed in SRIS 0101 revealed a result of 44.

The organohydrogenpolysiloxane A1, the methylvinylpolysiloxane B1, and the toluene solution of a chloroplatinic acid-olefin complex (platinum content: 0.5%) were mixed together in the same proportions as those used above in preparing the silicone elastomer spherical microparticles, and the resulting mixture was poured onto a Teflon (a registered trademark) tray in an amount sufficient to generate a thickness of approximately 1 mm. The mixture was left to stand at 25° C. for 24 hours, and was then heated for 1 hour in a thermostatic chamber at 50° C., thus forming a silicone elastomer sheet. Test pieces were prepared by cutting the obtained sheet into square pieces with a length along one side of approximately 30 mm, and following measurement of the mass of these test pieces, each test piece was immersed for 24 hours in one of the oil substances shown in Table 1. This caused the test piece to absorb the oily substance and swell. Each test piece was then removed from the oily substance, and following removal of any oily substance on the test piece surface by wiping with a tissue, the mass of the test piece was re-measured. Table 1 lists the amount of the oily substance absorbed (the oil absorption amount) by the silicone elastomer sheet per 1 g of the silicone elastomer.

5.0 g of the silicone microparticles obtained in the manner described above and 50 g of an oily substance shown in Table 1 were placed in a 100 ml glass bottle, and after shaking for 30 minutes, the bottle was left to stand for 3 days at room temperature. A solid-liquid separation was then performed using pressure filtration, and the mass of the resulting cake-like solid fraction was measured. Table 1 lists the oil absorption amount per 5 g of the silicone microparticles, which was calculated using the formula: [mass (g) of solid fraction following solid-liquid separation]−5.0 (g).

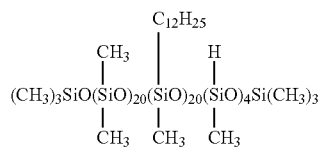

(3)

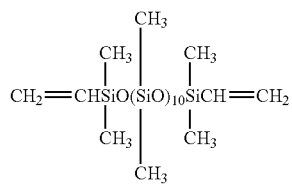

(4)

Example 2

A water dispersion of silicone elastomer microparticles was obtained in the same manner as example 1, with the exceptions of replacing the 400 g of the organohydrogenpolysiloxane A1 with 400 g of an organohydrogenpolysiloxane A2 represented by formula (5) shown below and having an amount of long-chain monovalent hydrocarbon groups of 10.5 mol % and a viscosity of 130 mm$^2$/s, altering the amount of the methylvinylpolysiloxane B1 from 114 g to 113 g (equivalent to 0.91 olefinic unsaturated groups within the methylvinylpolysiloxane B1 per SiH group within the organohydrogenpolysiloxane A2), and altering the amount of water added immediately prior to obtaining the uniform white emulsion from 382 g to 383 g. Inspection of the shape of these silicone elastomer microparticles in the same manner as example 1 revealed spherical particles, and measurement of the volume average particle diameter in the same manner as example 1 yielded a result of 12 µm.

Using 876 g of the obtained water dispersion of silicone elastomer spherical microparticles as a raw material, a hydrolysis-condensation reaction and subsequent dewatering were conducted in the same manner as example 1, thus forming microparticles with good flowability. During this process, the pH of the liquid upon addition of the 1,988 g of water and 57 g of 28% ammonia water was 11.2, and the amount of the polyorganosilsesquioxane following the hydrolysis-condensation reaction was 8.7 parts by mass per 100 parts by mass of the silicone elastomer spherical microparticles. Inspection of the obtained microparticles using an electron microscope revealed spherical particles, the surface of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as example 1, yielding a result of 12 µm.

With the exception of using the organohydrogenpolysiloxane A2 instead of the organohydrogenpolysiloxane A1, a non-sticky silicone elastomer was obtained in the same manner as example 1. Measurement of the hardness of this silicone elastomer using an Asker C hardness meter prescribed in SRIS 0101 yielded a result of 53.

With the exception of using the organohydrogenpolysiloxane A2 instead of the organohydrogenpolysiloxane A1, preparation of a silicone elastomer sheet and measurement of the oil absorption amounts for the sheet were conducted in the same manner as example 1. The oil absorption amounts listed in Table 1 represent absorption amounts per 1 g of the silicone elastomer.

The oil absorption amounts for 5.0 g samples of the obtained silicone microparticles were measured in the same manner as example 1. Table 1 lists the oil absorption amounts, which were calculated using the formula: [mass (g) of solid fraction following solid-liquid separation]−5.0 (g).

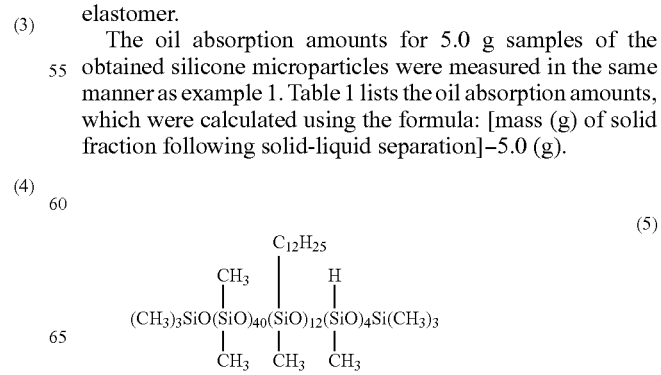

(5)

Comparative Example 1

A glass beaker with a capacity of 1 liter was charged with 19 g of a methylhydrogenpolysiloxane A3 represented by formula (6) shown below, containing no long-chain monovalent hydrocarbon groups and having a viscosity of 30 mm$^2$/s, and 500 g of a methylvinylpolysiloxane B2 represented by a formula (7) shown below, containing no long-chain monovalent hydrocarbon groups and having a viscosity of 580 mm$^2$/s (equivalent to 0.95 olefinic unsaturated groups within the methylvinylpolysiloxane B2 per SiH group within the methylhydrogenpolysiloxane A3), and stirring and mixing were performed at 2,000 rpm using a homomixer. To the resulting mixed liquid were added 1.2 g of a polyoxyethylene lauryl ether (number of mols of added ethylene oxide=9 mol) and 100 g of water, and subsequent stirring at 6,000 rpm using the homomixer yielded an O/W type emulsion of increased viscosity. Stirring was continued for a further 15 minutes. Subsequently, with the stirring continued at 2,000 rpm, 377 g of water was added, yielding a uniform white emulsion. This emulsion was transferred to a glass flask with a capacity of 1 liter fitted with a stirring device having an anchor-shaped stirring blade, and following adjustment of the temperature to a value of 15 to 20° C., a mixed solution containing 0.8 g of a toluene solution of a chloroplatinic acid-olefin complex (platinum content: 0.5%) and 1.8 g of a polyoxyethylene lauryl ether (number of mols of added ethylene oxide=9 mol) was added to the flask under constant stirring. Stirring was then continued at the same temperature for 12 hours, thus forming a water dispersion of silicone elastomer microparticles. Inspection of the shape of these silicone elastomer microparticles under an optical microscope revealed that the particles were spherical, and measurement of the volume average particle diameter using a Multisizer 3 yielded a result of 12 µm.

1,155 g of the thus obtained water dispersion of silicone elastomer spherical microparticles was transferred to a glass flask with a capacity of 3 liters fitted with a stirring device having an anchor-shaped stirring blade, and 1,734 g of water and 60 g of 28% ammonia water were added to the flask. The pH of the liquid at this point was 11.3. Following lowering of the temperature to 5 to 10° C., 50.7 g of methyltrimethoxysilane (an amount that yields 4.2 parts by mass of a polymethylsilsesquioxane following the hydrolysis, and condensation reaction per 100 parts by mass of the silicone elastomer spherical microparticles) was added dropwise to the flask over a period of 20 minutes, and stirring was then continued for a further 1 hour. During this period, the liquid temperature was maintained at 5 to 10° C. Subsequently, the reaction mixture was heated to 55 to 60° C., and stirring was continued at this temperature for 1 hour to complete the hydrolysis-condensation reaction of the above methyltrimethoxysilane.

The thus obtained methyltrimethoxysilane hydrolysis-condensation reaction liquid was dewatered in the same manner as example 1, yielding microparticles with good flowability. Inspection of these microparticles using an electron microscope revealed spherical particles, the surface of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as example 1, yielding a result of 12 µm.

With the exceptions of using the organohydrogenpolysiloxane A3 instead of the organohydrogenpolysiloxane A1, and using the methylvinylpolysiloxane B2 instead of the methylvinylpolysiloxane B1, a non-sticky silicone elastomer was obtained in the same manner as example 1. Measurement of the hardness of this silicone elastomer using an Asker C hardness meter prescribed in SRIS 0101 yielded a result of 55.

With the exceptions of using the organohydrogenpolysiloxane A3 instead of the organohydrogenpolysiloxane A1, and using the methylvinylpolysiloxane B2 instead of the methylvinylpolysiloxane B1, preparation of a silicone elastomer sheet and measurement of the oil absorption amounts for the sheet were conducted in the same manner as example 1. The oil absorption amounts listed in Table 1 represent absorption amounts per 1 g of the silicone elastomer.

The oil absorption amounts for 5.0 g samples of the obtained silicone microparticles were measured in the same manner as example 1. Table 1 lists the oil absorption amounts, which were calculated using the formula: [mass (g) of solid fraction following solid-liquid separation]−5.0 (g).

TABLE 1

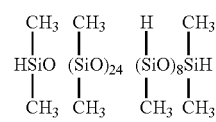

(6)

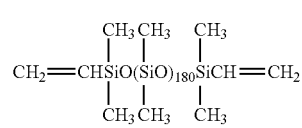

(7)

| Item | | Example 1 | Example 2 | Comparative example 1 |
|---|---|---|---|---|
| Silicone elastomer oil absorption amount [g/1 g of silicone elastomer] | Squalane* | 1.6 | 0.7 | 0.1 or less |
| | Liquid paraffin | 0.7 | 0.4 | 0.1 or less |
| | Octyl palmitate | 1.5 | 0.7 | 0.2 |
| | Isocetyl myristate | 1.1 | 0.6 | 0.1 or less |
| | Isocetyl isostearate | 1.0 | 0.5 | 0.1 or less |

TABLE 1-continued

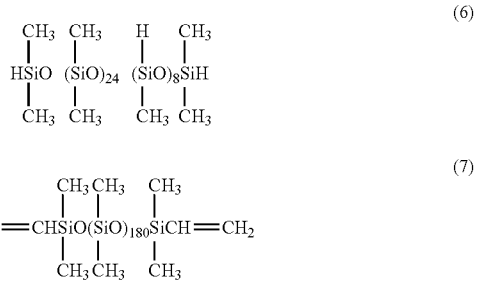

| Item | | Example 1 | Example 2 | Comparative example 1 |
|---|---|---|---|---|
| Microparticles oil absorption amount [g/5 g of microparticles] | Squalane* | 15 | 10 | 5 |
| | Liquid paraffin | 10 | 8 | 5 |
| | Octyl palmitate | 11 | 7 | 2 |
| | Isocetyl myristate | 7 | 6 | 4 |
| | Isocetyl isostearate | 7 | 6 | 4 |

*Squalane was used as a substitute for sebum.

The silicone microparticles of example 1 and example 2 exhibited properties that enabled the absorption of large amounts of sebum and liquid oils composed of hydrocarbon oils and ester oils, and can therefore be expected to provide effects such as suppression of changes in cosmetic make-up properties caused by sebum, suppression of changes in the color of cosmetic materials, and prevention of shininess of cosmetic materials, as well as other effects such as suppression of the greasiness, stickiness, and oily film feeling of cosmetic materials containing an added liquid oil such as a paraffin or ester. In contrast, the silicone microparticles of comparative example 1 exhibited only minimal absorption of sebum and liquid oils composed of hydrocarbon oils and ester oils, meaning the effects mentioned above cannot be expected.

What is claimed is:

1. Silicone microparticles, comprising 100 parts by mass of silicone elastomer spherical microparticles having a volume average particle diameter within a range from 0.1 to 100 μm, and 0.5 to 25 parts by mass of a polyorganosilsesquioxane that coats a surface of the silicone elastomer spherical microparticles,
   wherein the silicone elastomer is capable of absorbing not less than 30 parts by mass of at least one oily substance selected from the group consisting of sebum, hydrocarbon oils and ester oils per 100 parts by mass of the silicone elastomer,
   wherein the silicone elastomer is a cured product of a liquid silicone composition comprising:
   (A)
      (A1) an organohydrogenpolysiloxane having two hydrogen atoms bonded to silicon atoms within each molecule, represented by an average composition formula (1):

$$R^1_a H_b SiO_{(4-a-b)/2} \quad (1)$$

wherein $R^1$ represents an unsubstituted or substituted monovalent hydrocarbon group of 1 to 30 carbon atoms excluding aliphatic unsaturated groups, and a and b are positive numbers that satisfy $0<a<3$, $0<b\leq3$, and $0.1\leq a+b\leq3$, (A2) an organohydrogenpolysiloxane represented by the average composition formula (1) and having at least three hydrogen atoms bonded to silicon atoms within each molecule, or
      a combination of (A1) and (A2),
   (B)
      (B1) an organopolysiloxane having two monovalent olefinic unsaturated groups within each molecule, represented by an average composition formula (2):

$$R^2_c R^3_d SiO_{(4-c-d)/2} \quad (2)$$

wherein $R^2$ represents an unsubstituted or substituted monovalent hydrocarbon group of 1 to 30 carbon atoms excluding aliphatic unsaturated groups, $R^3$ represents a monovalent olefinic unsaturated group of 2 to 6 carbon atoms, and c and d are positive numbers that satisfy $0<c<3$, $0<d<3$, and $0.1<c+d<3$, (B2) an organopolysiloxane represented by the average composition formula (2) and having at least three monovalent olefinic unsaturated groups within each molecule, or
      a combination of component (B1) and component (B2), in an amount that yields from 0.5 to 2 monovalent olefinic unsaturated groups within component (B) per hydrogen atom bonded to a silicon atom within component (A), and
   (C) a platinum group metal-based catalyst,
   wherein from 5 to 70 mol% of at least one of $R^1$ of formula (1) and $R^2$ of formula (2) are monovalent hydrocarbon groups of 6 to 30 carbon atoms,
   provided that when component (A) is component (A1), component (B) is either component (B2) or a combination of component (B1) and component (B2).

2. The silicone microparticles according to claim 1, wherein a viscosity of component (A) is not more than 100,000 mm²/s.

3. The silicone microparticles according to claim 1, wherein a viscosity of component (B) is not more than 100,000 mm²/s.

4. The silicone microparticles according to claim 1, wherein a rubber hardness of the silicone elastomer, measured using an Asker C hardness meter prescribed in the Society of Rubber Industry, Japan Standard 0101, is within a range from 10 to 95.

5. The silicone microparticles according to claim 1, wherein the polyorganosilsesquioxane comprises an alkyl group that is substituted with an unsubstituted or substituted amino group.

6. The silicone microparticles according to claim 1, wherein the polyorganosilsesquioxane comprises units represented by a formula $R^4SiO_{3/2}$, wherein $R^4$ represents an unsubstituted or substituted monovalent hydrocarbon group of 1 to 20 carbon atoms.

7. The silicone microparticles according to claim 6, wherein not less than 50 mol% of all $R^4$ groups within the polyorganosilsesquioxane are methyl groups.

8. The silicone microparticles according to claim 6, wherein not more than 20 mol% of all $R^4$ groups within the polyorganosilsesquioxane are alkyl groups that are substituted with an unsubstituted or substituted amino group.

9. A method of producing the silicone microparticles defined in claim 1, the method comprising:
hydrolyzing and condensing an organotrialkoxysilane in a water medium, in presence of silicone elastomer spherical microparticles having a volume average particle diameter within a range from 0.1 to 100 μm and an alkaline material, thereby coating a surface of the silicone elastomer spherical microparticles with a polyorganosilsesquioxane, wherein
the silicone elastomer is capable of absorbing not less than 30 parts by mass of at least one oily substance selected from the group consisting of sebum, hydrocarbon oils and ester oils per 100 parts by mass of the silicone elastomer.

10. The method according to claim 9, wherein the organotrialkoxysilane is represented by a formula $R^4Si(OR^5)_3$, wherein $R^4$ represents an unsubstituted or substituted monovalent hydrocarbon group of 1 to 20 carbon atoms, and $R^5$ represents an unsubstituted monovalent hydrocarbon group of 1 to 6 carbon atoms.

11. A method of absorbing at least one oily substance selected from the group consisting of sebum, hydrocarbon oils and ester oils, the method comprising:
bringing the oily substance into contact with the silicone microparticles defined in claim 1, and
absorbing the oily substance into the silicone microparticles.

12. The silicone microparticles according to claim 1, wherein from 5 to 60 mol% of at least one of $R^1$ of formula (1) and $R^2$ of formula (2) are monovalent hydrocarbon groups of 6 to 30 carbon atoms.

13. The silicone microparticles according to claim 1, wherein from 5 to 22.2 mol% of at least one of $R^1$ of formula (1) and $R^2$ of formula (2) are monovalent hydrocarbon groups of 6 to 30 carbon atoms.

\* \* \* \* \*